United States Patent [19]
Bell

[11] Patent Number: 4,783,412
[45] Date of Patent: Nov. 8, 1988

[54] HYBRID DNA SYNTHESIS OF EPIDERMAL GROWTH FACTOR

[75] Inventor: Graeme I. Bell, San Francisco, Calif.

[73] Assignee: Chiron Corporation, Emeryville, Calif.

[21] Appl. No.: 58,706

[22] Filed: Jun. 3, 1987

Related U.S. Application Data

[63] Continuation of Ser. No. 821,873, Jan. 24, 1986, abandoned, which is a continuation of Ser. No. 511,372, Jul. 5, 1983, abandoned.

[51] Int. Cl.$^4$ .................. C12N 5/00; C12N 15/00; C12P 21/02; C12P 19/34
[52] U.S. Cl. .................................. 435/240.1; 435/70; 435/91; 435/172.1; 435/172.3; 435/253; 435/255; 435/320; 536/27; 935/13; 935/69; 935/70; 935/72
[58] Field of Search ............... 435/6, 68, 70, 71, 91, 435/172.1, 172.3, 240.1, 240.2, 240.23, 240.25, 240.4, 240.45, 240.46, 240.47, 317.1, 320, 243, 253, 255, 256; 536/27; 935/13, 29, 31, 32, 60, 69, 70, 71, 72, 73, 74

[56] References Cited

U.S. PATENT DOCUMENTS 4,719,180  1/1988  Eaton et al. ...................... 435/320

FOREIGN PATENT DOCUMENTS 0046039  2/1982  European Pat. Off. ............. 935/13

OTHER PUBLICATIONS

Cantanzaro et al., "Immunoscreening of Expression Clones Using Antibodies to Renin, EGF and NGF", Chem. Abstr., 100:30432t (1984) of *Manipulation Expression Genes Eukaryotes, Proc. Int. Conf., Int. Congr. Biochem.*, 12th (1982, Pub. 1983), 11–12.

Lawn et al., "The Isolation and Characterization of Linked Delta- and Beta-Globin Genes from a Cloned Library of Human DNA", Cell 15: 1157 (1978).

Myers et al., "Cloning a cDNA for the Pro-Alpha2 Chain of Hyman Type I Collagen", Proc. Natl. Acad. Sci., U.S.A. 78: 3516 (1981).

Houghton et al., "The Amino-Terminal Sequence of Human Fibroblast Interferon as Deduced from Reverse Transcripts Obtained Using Synthetic Oligonucleotide Primers", Nucleic Acids Res. 8: 1913 (1980).

Frey et al., "The Biosynthetic Precursor of Epidermal Growth Factor and the Mechanism of Its Processing", Proc. Natl. Acad. Sci. U.S.A. 76: 6294 (1979).

Scott et al.: Science 221, 236 (1983).

Britten et al.: Quarterly Rev. Biol. 46, 111 (1971).

Gray et al.: Nature 303, 722 (1983).

Bell et al., (1986), Nucleic Acids Research 14:21:8427–8446.

*Primary Examiner*—James Martinell
*Attorney, Agent, or Firm*—Ciotti & Murashige, Irell & Manella

[57] ABSTRACT

DNA sequences and methods of obtaining DNA sequences which include a sequence encoding for mammalian epidermal growth factor are provided. The DNA sequences may be used in cloning and expression vectors for production of DNA and RNA and for producing polypeptides including mammalian epidermal growth factor.

*E. coli* strains HB 101 (pmegf1) and HB 101 (pmegf10b), and bacteriophage λhEGF34 were deposited at the A.T.C.C. on May 10, 1983 and given Accession Nos. 39357, 39358 and 40070, respectively.

5 Claims, No Drawings

HYBRID DNA SYNTHESIS OF EPIDERMAL GROWTH FACTOR

This application is a continuation of application Ser. No. 821,873, filed Jan. 24, 1986, now abandoned, which is a continuation of application Ser. No. 511,372, filed July 5, 1983, now abandoned.

BACKGROUND OF THE INVENTION

1. Field of the Invention

Epidermal growth factor (EGF) is a polypeptide of 53 amino acids that has been characterized in both mice and humans. It is a potent mitogen for a variety of cells, such as fibroblasts, glia, epithelial, endothelial and epidermal cells, both cultured and in vivo. EGF is also a potent inhibitor of gastric acid secretion. EGF was first isolated from male mouse submaxillary glands, where it exists in inexplicably high levels.

In glandular homogenates, EGF is found as a 74,000 dalton complex of two molecules of EGF (Mr 6045) and two molecules of a binding protein (Mr 29,300), a kallikrein-like arginyl enteropeptidase The amino acid sequence of mouse submaxillary EGF has been determined and the synthesis of EGF and a larger 9000 dalton precursor with a carboxy terminal extension has been demonstrated in cultured submaxillary glands.

Human EGF, which appears to be similar if not identical to urogastrone, is also found in urine in larger forms of 28,000 and 30,000 Daltons that do not dissociate on sodium dodecyl sulfate-polyacrylamide gel electrophoresis.

Isolating both the DNA or RNA encoding for EGF and particularly a putative EGF precursor protein is extremely difficult for a number of reasons. Even where the peptide is abundant, the amount of messenger RNA is extremely small. Immunoprecipitation of in vitro translation products, even under strongly denaturing conditions fails to detect a precursor protein, possibly due to the huge size of the precursor and/or the masking of its antigenic determinants on the native peptide to which antibodies were made. Because of the physiological importance of EGF there is substantial interest in being able to obtain DNA sequences encoding for EGF and the EGF polypeptide precursor. In addition, since it is known that a number of hormones are generated by proteolytic processing from larger precursors the cDNA and derived amino acid sequence of the EGF precursor could reveal "cryptic", previously unknown polypeptide hormones and/or growth factors.

2. Description of the Prior Art

A human genomic cDNA library in bacteriophage λ is described in Lawn et al., *Cell* (1978) 15:1157–1174. Savage et al., *J. Biol. Chem.* (1972) 247:7612–7621 report the amino acid sequence of mouse EGF. Sporn et al., *Science* (1983) 219:1329–1331 and Assoian et al., *J. Biol. Chem.* (1983) 258:7155–7160 describe transforming growth factors (TGF). See particularly Gray et al., *Nature* (1983) 303:722–725.

SUMMARY OF THE INVENTION

DNA and RNA are provided encoding for mammalian EGF, polypeptide precursors thereof, and numerous other polypeptides also encoded for by the DNA sequence which includes the segment encoding for EGF. The DNA sequences may be used for production of mammalian EGF, precursors of mammalian EGF, and associated related polypeptides. Employing radiolabeled hybridization probes, messenger RNA encoding for the mouse EGF precursor is detected, isolated and used for the production of cDNA. The cDNA is sequenced and a fragment employed for hybridization with human DNA under conditions where mismatched heterologous hybrids can be detected. In this manner, a DNA sequence encoding for a large precursor peptide encompassing human EGF or urogastrone and numerous, related polypeptides is detected and isolated.

DESCRIPTION OF SPECIFIC EMBODIMENTS

In accordance with the subject invention, DNA and RNA sequences are provided which include a segment encoding for EGF, particularly mouse and human, as well as the expression products of these sequences, including propolypeptides and peptides, particularly peptides having one or more physiological functions of EGF, or peptides having one or more other hormonal or growth factor regulatory functions.

The DNA sequences of interest are single or double stranded ranging from about 60 bases or base pairs (bp) to about 5 thousand base pairs (kbp), where sequences encoding for a physiologically active polypeptide will generally range from about 60 bp to about 1000 bp, which may include introns. Generally, the DNA sequences will have open reading frames (involving one or more exons) encoding for polypeptides ranging from about 20 amino acids to polypeptides about 1000 amino acids, where the sequence will include at least 2, usually at least 5, more usually at least 10 bp, outside the segment encoding EGF. Polypeptides of particular interest will generally be of from about 20 to 250 amino acids, more usually from about 20 to 175 amino acids, particularly 30 to 60 amino acids.

The DNA segments encoding for polypeptides of interest or mature polypeptides may be located in any region in the DNA sequences described in this invention. Of particular interest are sequences bordered by basic amino acids, i.e. arginine and lysine, more particularly when joined to a second basic amino acid, or alanine, leucine, aspartic or glutamic acid or amide thereof. Amongst these sequences of interest are seven previously unknown EGF-like polypeptides with amino acid sequences homologous to EGF. The DNA sequences obtained in accordance with this invention were obtained by the following experimental design.

A mammalian cDNA or genomic DNA library is screened with a plurality of radiolabeled hybridization probes for detection of a sequence encoding for an amino acid sequence present in EGF. A plurality of probes are employed providing for the various possible redundant codons encoding for the oligopeptide. In the subject method a cDNA library from mouse submaxillary gland cells was probed. Plasmids binding strongly to the probes are isolated and the several overlapping cDNA inserts sequenced. The mouse EGF encoding cDNA has about 4800 bases. Mouse EGF is encoded for by nucleotides 3281–3440±5, with an open reading frame encoding for 1217±5 amino acid residues and a protein of approximately 130–140 kilodaltons (kdal), particularly about 133 kdal.

The mouse cDNA may then be used to probe a human cDNA or genomic DNA bank. Conveniently a restriction fragment may be employed of about 500 to 1500 bp. Particularly, a BstEII-PvuII fragment of about 1213±5 bp, may be employed The hybridization is carried out under conditions which facilitate the detection of mismatched, heterologous hybrids. The BstEII- PvuII fragment encodes mouse EGF (53 amino acids) and 286 amino acids before and 66 amino acids after the EGF moiety Clones which hybridized to the probe were isolated and the human DNA inserts characterized.

Once the DNA sequence is isolated, it can be used in a variety of ways: For production of synthetic DNA sequences, either in whole or in part, for replication, or for the production of messenger RNA or expression of the precursor protein incorporating EGF, fragments of such protein or of EGF, or analogs of EGF, differing by one or more amino acids, usually by not more than about five amino acids from the naturally occurring EGF amino acid sequence.

Various DNA sequences are of particular interest in encoding polypeptides which can be obtained from the cDNA sequence. These DNA sequences are set forth in the argument map set forth in the experimental section, along with the human EGF sequence. The polypeptide sequences of interest include, but are not limited to, seven previously undescribed, EGF-like polypeptides identified on the basis of the homology of their amino acid sequences to EGF, especially the positional relationship(s) of the several cysteine residues. (See diagram in experimental section.) These sequences are frequently bounded by one or more basic amino acids.

Once the desired DNA sequence encoding for a protein or peptide of interest, e.g. EGF or its homologues, has been isolated, it can be joined with other DNA sequences for replication and expression. A wide variety of vectors are available for unicellular microorganisms, particularly for bacteria and fungi, where the DNA sequence encoding the poly(amino acid) of interest may be replicated and/or expressed.

Various hosts of interest include *E. coli, S. cerevisiae, B, subtilis,* mouse 3T3 cells, or the like. Conventional vectors include replication systems derived from R6-5, ColEI, the 2 μm plasmid from yeast, RK plasmids, or the like. Alternative replication systems may be derived from viruses or phage, such as lambda, SV40, etc. In some instances, it will be desirable to have two different replication systems, where different functions may be achieved in different hosts. These vectors, referred to as shuttle vectors, frequently employ a replication system for *E. coli* and a replication system for a higher organism, e.g. yeast, so that amplification of the gene or cloning may be achieved in the bacterium, while expression may be achieved in the higher organism with appropriate processing, e.g. glycosylation.

Conveniently included with the replication system is at least one marker, which allows for selection or selective pressure to maintain the DNA construct containing the subject DNA sequence in the host. Convenient markers include biocidal resistance, e.g. antibiotics, heavy metals and toxins; complementation in an auxotrophic host; immunity; etc. The DNA sequence including the fragment encoding for a polypeptide having epidermal growth factor physiological properties or fragments of such sequence may be replicated in a cloning vector, which is capable of replication in a unicellular microorganism, such as bacteria and yeast. The DNA may also be used in an expression vector for expression of a polypeptide of interest, which may be mammalian EGF, particularly mouse or human, other physiologically active polypeptides present in the sequence, e.g. other hormones or growth factors, fragments thereof or analogs thereof differing by from about one to five amino acids.

The open reading frame of the DNA sequence allows for the production of a large polypeptide. The large polypeptide may be treated in a variety of ways. The large polypeptide may be partially digested with a variety of proteases either individually or in combination. Illustrative endopeptidases include trypsin, pepsin, membrane dipeptidases, esteropeptidases or the like. The resulting fragments may then be separated by charge and/or molecular weight by any conventional means, e.g. filtration, sedimentation, chromatography, electrophoresis, or the like and then tested for physiological activity. Of particular interest are growth factors acting as mitogens or differentiation regulators. Based on the activities observed, the various fractions may be further purified by bioassays to obtain pure active factors.

The DNA sequences of this invention can be used in a variety of ways. Fragments can be used as probes for detecting complementary sequences in genomic DNA or in messenger RNA for detecting mutations and/or deletions in genomic DNA of hosts. The sequences can be used for expressing the polypeptides encoded for by the sequence.

The following examples are offered by way of illustration and not by way of limitation:

EXPERIMENTAL

Methods cDNA Synthesis and Construction of Recombinant Plasmids

To construct the cDNA library, polyA-containing RNA was isolated from the submaxillary glands of 60-day-old male Swiss-Webster mice. ds cDNAs were prepared and inserted into the PstI site of a pBR322 derivative using the dGdC tailing technique (Chirgwin et al., *Biochemistry* (1979) 18:5294–5299; Goodman and MacDonald, *Methods in Enzymol.* (1980) 68:75–90). Resultant tetracyline-resistant transformants of *E. coli* HB101 were stored at −70° C. in microtiter dishes (Gergen et al., *Nucl. Acids Res.* (1979) 7:2115–2136; Ish-Horowicz and Burke, *ibid.* (1981) 9:2989–2998).

Oligonucleotides were then synthesized by solid-phase phosphoramidite methodology as described in copending application, Ser. No. 457,412, followed by isolation from 20% acrylamide gels modification of the method described in Beancage and Camthers, Tetrahedron Lett. (1981) 22: 1859–1862. Dodecamers were prepared which were complementary to the strand coding for amino acids 17 to 23 (lacking the last 5'-nucleotide) of mouse EGF cDNA. The fractions had the following sequences, where after the addition of the eleventh nucleotide, two pools were prepared, one terminating in A and the other terminating in G and after addition of the seventeenth nucleotide, the two pools were further divided with addition of the eighteenth nucleotide, with two of the pools now terminating in G and the other two pools terminating in A. In this manner, a total of four pools were obtained, where each pool had a plurality of eicosamers of differing compositions at positions 3, 6 and 9.

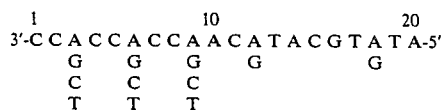

The different sequences are required because of the uncertainty as to the specific codon usage due to the redundancy of the genetic code for amino acids.

Synthetic oligonucleotides were labeled with adenosine 5'-($\gamma$-$^{32}$P) triphosphate (ICN, crude preparation, 7000 Ci/mmol, 1Ci=3.7×10$^{10}$ Bq) by a polynucleotide kinase reaction (Wallace et al., *Nucl. Acids Res.* (1981) 9:879-894). The labeled oligonucleotides were separated from unincorporated ($\gamma$-$^{32}$P) triphosphates by chromatography on a C-18 Sep-Pak ™ column (Waters Associates, Inc.) as follows: The crude labeling mixture was applied (disposable syringe) to the Sep-Pak cartridge which was then washed wtih 20 ml of water to elute the unincorporated adenosine 5'-($\gamma$-$^{32}$P) triphosphate. The radiolabeled oligonucleotide was then eluted with 1:1 (v/v) methanol: 0.1M triethylammonium acetate (pH 7.3) and the eluate evaported to dryness. The specific activity of the probe was of the order of 10$^8$-10$^9$ cpm/$\mu$g.

Transformants were grown on Whatman 541 filter paper, the plasmids amplified in situ with chloramphenicol and the DNA immobilized on the filters (Gergen et al., supra). $^{32}$P end-labeled probes were used to search the library. Additional screening was with nick translated cloned cDNA, with the same filters being used repeatedly.

The sequence of cDNA inserts were determined by the Maxam and Gilbert method.

mRNA Size Estimation

Glyoxylated total RNA from male and female mouse submaxillary glands was separated on 2% agarose gels, transferred to nitrocellulose and hybridized with a nick translated $^{32}$P-labeled PstI-PstI fragment of the EGF cDNA insert. After washing, the RNA was autoradiographed at −b 70° C. using an intensifying screen. Glyoxylated HindIII $\lambda$ and $\phi$174 RF HaeIII digest DNA fragments were used as size markers.

Results

Screening of the cDNA Library 5000 transformants were initially screened, where colonies yielded strong signals with pool 4 probes, t pools having the nucleotides at positions 12 and 18 of and A, respectively. Weaker, but definitely positi signals were obtained with pool 3 which had the nuc otides G and G, respectively. Pools 1 and 2 gave positive signals. The largest clone was 1800 bp. Terr nal restriction and other fragments of this clone we used to screen the original 5000 plus 7500 additior colonies (12,500 total) and yielded additional overle ping cDNA colonies which did not contain the EC sequence. Since it was subsequently determined DNA sequence analysis (*vide infra*) that these overle ping clones lacked the 5'-terminal region of the mRN another cDNA library was synthesized using an olig nucleotide primer complementary to nucleotid 1032-1051 (see argument map, infra) as follows:

3'-CCGCTTCCTTCGGTGCGAAT-5' and this library was then screened as described abo The relative abundance of the cDNA clones in 1 initial library suggests that EGF mRNA compri about 0.2% of the polyA+mRNA from this tissue.

mRNA Sequence

The size of mouse EGF mRNA was determined Northern analysis of mRNA from adult male and male glands to be about the same size as 28s ribosor RNA, approximately 4800 bases. The mRNA in 1 male gland was at least ten-fold greater in abundar than in the female gland. The nucleotide sequence overlapping cDNA clones provided 4750 bp of quence as follows:

```
AAAAAAGGAGAAGGGAUUCCUAUCUGUAUAUAGGGAAGGAAUCCUAUCUGCAUAUUUCGUUCUUAGCACCAUCCCUCAUCCCGGUGGGCUUGUAACUUUCCAUCAAUGCUUGUCUGUCU        119

CGUUUCUCUUUCAUCCUUUGCCUGGUUGUGCCUGUCUCAGGGAGAAAUCAGUCACCUGCAGGCCUUGCAGGGCUCUUAGGCUCUGGGAAAUUUGUCAUACGGUGUCAGGUACUUCUUA            238

1
                                                                                                                        Met
UUGCUGUCCAAAGGGCAAAAAAAAAGUGAGACAAAGAACUCUCCCGGAGCCUUUCCGGCUGCACUCAGAGGCUCUCGAGAGCUGCAGGAGGACCUGCAAAGCCAGCUAAAUAAAAG AUG        356
                                                                                                                  A
                    10                              20                  Phe          30
Pro Trp Gly Arg Arg Pro Thr Trp Leu Leu Leu Ala Phe Leu Leu Val Phe Leu Lys Ile Ser Ile Leu Ser Val Thr Ala Trp Gln Thr
CCC UGG GGC CGA AGG CCA ACC UGG UUG UUG CUC GCC UUC CUG CUG GUG UUU UUA AAG AUU AGC AUA CUC AGC GUC ACA GCA UGG CAG ACC        446
                                 C                                                                       U
                40                             50                            60
Gly Asn Cys Gln Pro Gly Pro Leu Glu Arg Ser Glu Arg Ser Gly Thr Cys Ala Gly Pro Ala Pro Phe Leu Val Phe Ser Gln Gly Lys
GGG AAC UGU CAG CCA GGU CCU CUC GAG AGA AGC GAG AGA AGC GGG ACU UGU GCC GGU CCU GCC CCC UUC CUA GUU UUC UCA CAA GGA AAG        536
                            70                           80                           90
Ser Ile Ser Arg Ile Asp Pro Asp Gly Thr Asn His Gln Gln Leu Val Val Asp Ala Gly Ile Ser Ala Asp Met Asp Ile His Tyr Lys
AGC AUC UCU CGG AUU GAC CCA GAU GGA ACA AAU CAC CAG CAA UUG GUG GUC GAU GCU GGC AUC UCA GCA GAC AUG GAU AUU CAU UAU AAA        626
                      100                          110                          120
Lys Glu Arg Leu Tyr Trp Val Asp Val Glu Arg Gln Val Leu Leu Arg Val Phe Leu Asn Gly Thr Gly Leu Glu Lys Val Cys Asn Val
AAA GAG AGA CUC UAU UGG GUC GAU GUA GAA AGA CAA GUU UUG CUA AGA GUU UUC CUU AAC GGG ACA GGA CUA GAG AAA GUG UGC AAU GUA        716
                     130                           140                         150
Glu Arg Lys Val Ser Gly Leu Ala Ile Asp Trp Ile Asp Asp Glu Val Leu Trp Val Asp Gln Gln Asn Gly Val Ile Thr Val Thr Asp
GAG AGG AAG GUG UCU GGG CUG GCC AUA GAC UGG AUA GAU GAU GAA GUU CUC UGG GUA GAC CAA CAG AAC GGA GUC AUC ACC GUA ACA GAU        806
                 160                       170       Asn                 180
Met Thr Gly Lys Asn Ser Arg Val Leu Leu Ser Ser Leu Lys His Pro Ser Asn Ile Ala Val Asp Pro Ile Glu Arg Leu Met Phe Trp
AUG ACA GGG AAA AAU UCC CGA GUU CUU CUA AGU UCC UUA AAA CAU CCG UCA AAU AUA GCA GUG GAU CCA AUA GAG AGG UUG AUG UUU UGG        896
                                                                      A
                190                         200                         210
Ser Ser Glu Val Thr Gly Ser Leu His Arg Ala His Leu Lys Gly Val Asp Val Lys Thr Leu Leu Glu Thr Gly Gly Ile Ser Val Leu
UCU UCA GAG GUG ACC GGC AGC CUU CAC AGA GCA CAC CUC AAA GGU GUU GAU GUA AAA ACA CUG CUG GAG ACA GGG GGA AUA UCG GUG CUG        986
                220                       230                        240
Thr Leu Asp Val Leu Asp Lys Arg Leu Phe Trp Val Gln Asp Ser Gly Glu Gly Ser His Ala Tyr Ile His Ser Cys Asp Tyr Glu Gly
ACU CUG GAU GUC CUG GAC AAA CGG CUC UUC UGG GUU CAG GAC AGU GGC GAA GGA AGC CAC GCU UAC AUU CAU UCC UGU GAU UAU GAG GGU        1076
                 250                     260                          270
Gly Ser Val Arg Leu Ile Arg His Gln Ala Arg His Ser Leu Ser Ser Met Ala Phe Phe Gly Asp Arg Ile Phe Tyr Ser Val Leu Lys
GGC UCC GUC CGU CUU AUC AGG CAU CAA GCA CGG CAC AGU UUG UCU UCA AUG GCC UUU UUU GGU GAU CGG AUC UUC UAC UCA GUG UUG AAA        1166
```

```
                                      280                                              290                                              300
Ser Lys Ala Ile Trp Ile Ala Asn Lys His Thr Gly Lys Asp Thr Val Arg Ile Asn Leu His Pro Ser Phe Val Thr Pro Gly Lys Leu
AGC AAG GCG AUU UGG AUA GCC AAC AAA CAC ACG GGG AAG GAC ACG GUC AGG AUU AAC CUC CAU CCA UCC UUU GUG ACA CCU GGA AAA CUG    1256

310                                              320                                              330
Met Val Val His Pro Arg Ala Gln Pro Arg Thr Glu Asp Ala Ala Lys Asp Pro Asp Pro Glu Leu Leu Lys Gln Arg Gly Arg Pro Cys
AUG GUA GUA CAC CCU CGU GCA CAG CCC AGG ACA GAG GAC GCU GCU AAG GAU CCU GAC CCC GAA CUU CUC AAA CAG AGG GGA AGA CCA UGC    1346

340                                              350                                              360
Arg Phe Gly Leu Cys Glu Arg Asp Pro Lys Ser His Ser Ser Ala Cys Ala Glu Gly Tyr Thr Leu Ser Arg Asp Arg Lys Tyr Cys Glu
CGC UUC GGU CUC UGU GAG CGA GAC CCU AAG UCC CAC UCG AGC GCA UGC GCU GAG GGC UAC ACG UUA AGC CGA GAC CGG AAG UAC UGC GAA    1436

370                                              380                                              390
Asp Val Asn Glu Cys Ala Thr Gln Asn His Gly Cys Thr Leu Gly Cys Glu Asn Thr Pro Gly Ser Tyr His Cys Thr Cys Pro Thr Gly
GAU GUC AAU GAA UGU GCC ACU CAG AAU CAC GGC UGU ACU CUU GGG UGU GAA AAC ACC CCU GGA UCC UAU CAC UGC ACA UGC CCC ACA GGA    1526

400                                              410                                              420
Phe Val Leu Leu Pro Asp Gly Lys Gln Cys His Glu Leu Val Ser Cys Pro Gly Asn Val Ser Lys Cys Ser His Gly Cys Val Leu Thr
UUU GUU CUG CUU CCU GAU GGG AAA CAA UGU CAC GAA CUU GUU UCC UGC CCA GGC AAC GUA UCA AAG UGC AGU CAU GGC UGU GUC CUG ACA    1616

430                                              440                                              450
Ser Asp Gly Pro Arg Cys Ile Cys Pro Ala Gly Ser Val Leu Gly Arg Asp Gly Lys Thr Cys Thr Gly Cys Ser Ser Pro Asp Asn Gly
UCA GAU GGU CCC CGG UGC AUC UGU CCU GCA GGU UCA GUG CUU GGG AGA GAU GGG AAG ACU UGC ACU GGU UGU UCA UCG CCU GAC AAU GGU    1706

460                                              470                                              480
Gly Cys Ser Gln Ile Cys Leu Pro Leu Arg Pro Gly Ser Trp Glu Cys Asp Cys Phe Pro Gly Tyr Asp Leu Gln Ser Asp Arg Lys Ser
GGA UGC AGC CAG AUC UGU CUU CCU CUC AGG CCA GGA UCC UGG GAA UGU GAU UGC UUU CCU GGG UAU GAC CUA CAG UCA GAC CGA AAG AGC    1796

490                                              500                                              510
Cys Ala Ala Ser Gly Pro Gln Pro Leu Leu Leu Phe Ala Asn Ser Gln Asp Ile Arg His Met His Phe Asp Gly Thr Asp Tyr Lys Val
UGU GCA GCU UCA GGA CCA CAG CCA CUU UUA CUG UUU GCA AAU UCC CAG GAC AUC CGA CAC AUG CAU UUU GAU GGA ACA GAC UAC AAA GUU    1886

520                                              530                                              540
Leu Leu Ser Arg Gln Met Gly Met Val Phe Ala Leu Asp Tyr Asp Pro Val Glu Ser Lys Ile Tyr Phe Ala Gln Thr Ala Leu Lys Trp
CUG CUC AGC CGG CAG AUG GGA AUG GUU UUU GCC UUG GAU UAU GAC CCU GUG GAA AGC AAG AUA UAU UUU GCA CAG ACA GCC CUG AAG UGG    1976

550                                              560                                              570
Ile Glu Arg Ala Asn Met Asp Gly Ser Gln Arg Glu Arg Leu Ile Thr Glu Gly Val Asp Thr Leu Glu Gly Leu Ala Leu Asp Trp Ile
AUA GAG AGG GCU AAU AUG GAU GGC UCC CAG CGA GAA AGA CUG AUC ACA GAA GGA GUA GAU ACG CUU GAA GGU CUU GCC CUG GAC UGG AUU    2066

580                                              590                                              600
Gly Arg Arg Ile Tyr Trp Thr Asp Ser Gly Lys Ser Val Val Gly Gly Ser Asp Leu Ser Gly Lys His His Arg Ile Ile Ile Gln Glu
GGC CGG AGA AUC UAC UGG ACA GAC AGU GGG AAG UCU GUU GUU GGA GGG AGC GAU CUG AGC GGG AAG CAU CAU CGA AUA AUC AUC CAG GAG    2156

610                                              620                                              630
Arg Ile Ser Arg Pro Arg Gly Ile Ala Val His Pro Arg Ala Arg Arg Leu Phe Trp Thr Asp Val Gly Met Ser Pro Arg Ile Glu Ser
AGA AUC UCG AGC CCG CGA GGA AUA GCU GUC CAU CCA AGG GCC AGG AGA CUG UUC UGG ACG GAC GUA GGG AUG UCU CCA CGG AUU GAA AGC    2246

640                                              650                                              660
Ala Ser Leu Gln Gly Ser Asp Arg Val Leu Ile Ala Ser Ser Asn Leu Leu Glu Pro Ser Gly Ile Thr Ile Asp Tyr Leu Thr Asp Thr
GCU UCC CUU CAA GGU UCC GAC CGG GUG CUG AUA GCC AGC UCC AAU CUA CUG GAA CCC AGU GGA AUC ACG AUU GAC UAC UUA ACA GAC ACU    2336

670                                              680                                              690
Leu Tyr Trp Cys Asp Thr Lys Arg Ser Val Ile Glu Met Ala Asn Leu Asp Gly Ser Lys Arg Arg Arg Leu Ile Gln Asn Asp Val Gly
UUG UAC UGG UGU GAC ACC AAG AGG UCU GUG AUU GAA AUG GCC AAU CUG GAU GGC UCC AAA CGC CGA AGA CUU AUC CAG AAC GAC GUA GGU    2426

700                                              710                                              720
His Pro Phe Ser Leu Ala Val Phe Glu Asp His Leu Trp Val Ser Asp Trp Ala Ile Pro Ser Val Ile Arg Val Asn Lys Arg Thr Gly
CAC CCC UUC UCU CUA GCC GUC UUU GAG GAU CAC CUG UGG GUC UCG GAU UGG GCU AUC CCA UCG GUA AUA AGG GUG AAC AAG AGG ACU GGC    2516

730                                              740                                              750
Gln Asn Arg Val Arg Leu Gln Gly Ser Met Leu Lys Pro Ser Ser Leu Val Val Val His Pro Leu Ala Lys Pro Gly Ala Asp Pro Cys
CAA AAC AGG GUA CGU CUU CAA GGC AGC AUG CUG AAG CCC UCG UCA CUG GUU GUG GUC CAU CCA UUG GCA AAA CCA GGU GCA GAU CCC UGC    2606

760                                              770                                              780
Leu Tyr Arg Asn Gly Gly Cys Glu His Ile Cys Gln Glu Ser Leu Gly Thr Ala Arg Cys Leu Cys Arg Glu Gly Phe Val Lys Ala Trp
UUA UAC AGG AAU GGA GGC UGU GAA CAC AUC UGC CAA GAG AGC CUG GGC ACA GCU CGG UGU UUG UGU CGU GAA GGU UUU GUG AAG GCC UGG    2696

790                                              800                                              810
Asp Gly Lys Met Cys Leu Pro Gln Asp Tyr Pro Ile Leu Ser Gly Glu Asn Ala Asp Leu Ser Lys Glu Val Thr Ser Leu Ser Asn Ser
GAU GGG AAA AUG UGU CUC CCU CAG GAU UAU CCA AUC CUG UCA GGU GAA AAU GCU GAU CUU AGU AAA GAC GUG ACA UCA CUG AGC AAC UCC    2786

820                                              830                                              840
Thr Gln Ala Glu Val Pro Asp Asp Gly Thr Glu Ser Ser Thr Leu Val Ala Glu Ile Met Val Ser Gly Met Asn Tyr Glu Asp Asp
ACU CAG GCU GAA GUA CCA GAC GAU GAU GGG ACA GAA UCU UCC ACA CUA GUG GCU GAA AUC AUG GUG UCA GGC AUG AAC UAU GAA GAU GAC    2876

850                                              860                                              870
Cys Gly Pro Gly Gly Cys Gly Ser His Ala Arg Cys Val Ser Asp Gly Glu Thr Ala Glu Cys Gln Cys Leu Lys Gly Phe Ala Arg Asp
UGU GGU CCC GGG GGU GUG GGA AGC CAU GCU CGA UGC GUU UCA GAC GGA GAG ACU GCU GAG UGU CAG UGU CUG AAA GGG UUU GCC AGG GAU    2966

880                                              890                                              900
Gly Asn Leu Cys Ser Asp Ile Asp Glu Cys Val Leu Ala Arg Ser Asp Cys Pro Ser Thr Ser Ser Arg Cys Ile Asn Thr Glu Gly Gly
GGA AAC CUG UGU UCU GAU AUA GAU GAG UGU GUG CUG GCU AGA UCG GAC UGC CCC AGC ACC UCG UCC AGG UGC AUC AAC ACU GAA GGU GGC    3056

910                                              920                                              930
Tyr Val Cys Arg Cys Ser Glu Gly Tyr Glu Asp Gly Ile Ser Cys Phe Asp Ile Asp Glu Cys Gln Arg Gly Ala His Asn Cys Ala
UAC GUC UGC AGA UGC UCA GAA GGC UAC GAA GAC GGG AUC UCC UGU UUC GAU AUU GAC GAG UGC CAG CGG GGG GCG CAC AAC UGC GCU    3146

940                                              950                                              960
Glu Asn Ala Ala Cys Thr Asn Thr Glu Gly Gly Tyr Asn Cys Thr Cys Ala Gly Arg Pro Ser Ser Pro Gly Arg Ser Cys Pro Asp Ser
GAG AAU GCC GCC UGC ACC AAC ACG GAG GGA GGC UAC AAC UGC ACC UGC GCA GGC CGC CCA UCC UCG CCC GGA CGC AGU UGC CCU GAC UCU    3236
                                                                                                              Human Gene     GAC UCU
                                                                                                                             Asp Ser 970                             Epidermal Growth Factor                                980
Thr Ala Pro Ser Leu Leu Gly Glu Asp Gly His His Leu Asp ::: Arg Asn Ser Tyr Pro Gly Cys Pro Ser Ser Tyr Asp Gly Tyr Cys Leu
ACC GCA CCC UCU CUC CUU GGG GAA GAU GGC CAC CAU UUG GAC ::: CGA AAU AGU UAU CCA GGA UGC CCA UCC UCA UAU GAU GGA UAC UGC CUC  3326
ACT CCA CCC CCG CAC CTC AGG GAA GAT GAC CAC CAC TAT TCC GTA AGA AAT AGT GAC TCT GAA TGT CCC CTG TCC CAC GAT GGG TAC TGC CTC
Thr Pro Pro Pro His Leu Arg Glu Asp Asp His His Tyr Ser Val Arg Asn Ser Asp Ser Glu Cys Pro Leu Ser His Asp Gly Tyr Cys Leu
```

```
                                    1000                                    1010                                   1020
Asn Gly Gly Val Cys Met His Ile Glu Ser Leu Asp Ser Tyr Thr Cys Asn Cys Val Ile Gly Tyr Ser Gly Asp Arg Cys Gln Thr Arg
AAU GGU GGC GUG UGC AUG CAU AUU GAA UCA CUG GAC AGC UAC ACA UGC AAC UGU GUU AUU GGC UAU UCU GGG GAU CGA UGU CAG ACU CGA    3416
CAT GAT GGT GTG TGC ATG TAT ATT GAA GCA TTG GAC AAG TAT GCA TGC AAC TGT GTT GTT GGC TAC ATC GGG GAC CGA TGT CAG TAC CGA
His Asp Gly Val Cys Met Tyr Ile Glu Ala Leu Asp Lys Tyr Ala Cys Asn Cys Val Val Gly Tyr Ile Gly Glu Arg Cys Gln Tyr Arg 1030                                    1040                                   1050
Asp Leu Arg Trp Trp Glu Leu Arg His Ala Gly Tyr Gly Gln Lys His Asp Ile Met Val Val Ala Val Cys Met Val Ala Leu Val Leu
GAC CUA CGA UGG UGG GAG CUG CGU CAU GCU GGC UAC GGG CAG AAG CAU GAC AUC AUG GUG GUG GCU GUC UGC AUG GUG GCA CUG GUC CUG    3506
GAC CTG AAG TGG TGG GAA CTG CGC CAC GCT GGC CAC GGG CAG CAG CAG AAG GTC ATC GTG GTG GCT GTC TGC GTG GTG GTG CTT GTC ATG
Asp Leu Lys Trp Trp Glu Arg His Ala Gly His Gly Gln Gln Gln Lys Val Ile Val Val Ala Val Cys Val Val Val Leu Val Met 1060                                    1070                                   1080
Leu Leu Leu Leu Gly Met Trp Gly Thr Tyr Tyr Tyr Arg Thr Arg Lys Gln Leu Ser Asn Pro Pro Lys Asn Pro Cys Asp Glu Pro Ser
CUG CUC CUC UUG GGG AUG UGG GGA ACU UAC UAC UAC AGG ACU CGG AAG CAG CUA UCA AAC CCC CCA AAG AAC CCU UGU GAU GAG CCA AGC    3596
CTG CTC CTC CTG AGC CTG TGG GGG GCC CAC TAC TAC AGG
Leu Leu Leu Leu Ser Leu Trp Gly Ala His Tyr Tyr Arg 1090                                    1100                                   1110
Gly Ser Val Ser Ser Ser Gly Pro Asp Ser Ser Ser Gly Ala Ala Val Ala Ser Cys Pro Gln Pro Trp Phe Val Val Leu Glu Lys His
GGA AGU GUG AGC AGC AGC GGG CCC GAC AGC AGC AGC GGG GCA GCU GUG GCU UCU UGU CCC CAA CCU UGG UUU GUG GUC CUA GAG AAA CAC    3686

1120                                    1130                                   1140
Gln Asp Pro Lys Asn Gly Ser Leu Pro Ala Asp Gly Thr Asn Gly Ala Val Val Asp Ala Gly Leu Ser Pro Ser Leu Gln Leu Gly Ser
CAA GAC CCC AAG AAU GGG AGU CUC CCU GCG GAU GGU ACG AAU GGU GCA GUA GUA GAU GCU GGC CUG UCU CCC UCC CUG CAG CUC GGG UCA    3776

1150                                    1160                                   1170
Val His Leu Thr Ser Trp Arg Gln Lys Pro His Ile Asp Gly Met Gly Thr Gly Gln Ser Cys Trp Ile Pro Pro Ser Ser Asp Arg Gly
GUC CAU CUG ACU UCA UGG AGA CAG AAG CCC CAC AUA GAU GGA AUG GGC ACA GGG CAA AGC UGC UGG AUU CCA CCA UCA AGU GAC AGA GGA    3866

1180                                    1190                                   1200
Pro Gln Glu Ile Glu Gly Asn Ser His Leu Pro Ser Tyr Arg Pro Val Gly Pro Glu Lys Leu His Ser Leu Gln Ser Ala Asn Gly Ser
CCC CAG GAA AUA GAG GGA AAC UCC CAC CUA CCC UCC UAC AGA CCU GUG GGG CCG GAG AAG CUG CAU UCU CUC CAG UCA GCU AAU GGA UCG    3956

1210              1217
Cys His Glu Arg Ala Pro Asp Leu Pro Arg Gln Thr Glu Pro Val Lys AM
UGU CAC GAA AGG GCU CCA GAC CUG CCA CGG CAG ACA GAG CCA GUU AAG UAG AAACUGGGAGUAGACAGAAGGACAGAAGGGAAAAAUAAACAAACCAUGCUGAUGA  4061

UGGUAGAGUGCUACAGACUUGGUACUCCAGUUCCACGGCUAAUCACUGCUCGCUCAGGGUCCUGAAGAUAGCUGCACAGCUGCAGAGCUGCACAGCGGGAUAGCUGCGACUUUUGCCUUC  4181

UUGCUUUAAGCAGUUCCAGUGAGAUACUCAAAAGAGAAGUGGAGAAAAAUCAUUAGAAACCAAAGUCAAGCAUUCAUAUAUAAGCUGUGUCUUCUUCACUGGACGGUUUGCCUCUUUUC  4301

CUUUUGCCUCAGAAGGAGUGGGUUAAAGCAGGUGACCCCAUGCUCUGUCAACCCCUGAAUAAAUGAUGUGAUCUACAUAGAAGUCUUUAGCUCACUCUCAGGAACGCUUGGAACACUAUAA  4421

CUUUUGCUAUGCAUAUACUGCCAAGUCUGGGCCCAUGCUCAUAAUUGUGCCUUCUGAAUUGUGAUAAAUUUAGUGAAAAAAACUGUAACUUAGAAUCUGAUUUAUUCAGGAUUAGAUCAUCUUU  4541

UUAUACUAUAAAAAUCUUCGAAUGAAAAAUAUUUAACUUUAAAAACAUUACCUUAAUCAUUGUCUUUUCUUCUUGAAGUCUUUCCCAGUGAAAACGCUCAAUUCUGCUGUUUCCAUAGAAU  4661

UUUUAAUUUAUUUUAAGACAUGAGAUUGUAAACAAAUUGCUUGAUUUUAUUUUAUCCUAAUUAUUUAAAUAAAAUCACCCUAAAGCAUCA                                 4750
```

```
                Arg Lys Tyr [Cys] Glu Asp Val Asn Glu [Cys] Ala Thr Gln Asn His [Gly] [Cys] Thr
                        Gln [Cys] His Glu Leu Val Ser [Cys] Pro Gly Asn Val Ser Lys [Cys] Ser
                        Thr [Cys] Thr Gly [Cys] Ser Ser Pro Asp Asn Gly Gly [Cys] Ser Gln
                        Lys Pro Gly Ala Asp Pro [Cys] Leu Tyr Arg Asn Gly [Gly] [Cys] Glu
        Met Val Ser Gly Met Asn Tyr Glu Asp Asp [Cys] Gly Pro Gly Gly [Cys] [Gly] Ser His
                                                            Ser Asp [Cys] Pro Ser
                                                    Gly Ala His Asn [Cys] Ala Glu Asn
        Asn Ser Tyr Pro Gly [Cys] Pro Ser Ser Tyr Asp Gly Tyr [Cys] Leu Asn [Gly] Gly Val

Leu Gly [Cys] Glu Asn [Thr] Pro [Gly] Ser [Tyr] His [Cys] Thr [Cys] Pro Thr [Gly] Phe Val Leu
        His Gly [Cys] Val Leu [Thr] Ser Asp Gly Pro Arg [Cys] Ile [Cys] Pro Ala [Gly] Ser Val Leu
        Ile [Cys] Leu Pro Leu Arg Pro [Gly] Ser Trp Glu [Cys] Asp [Cys] Phe Pro [Gly] Tyr Asp Leu
        His Ile [Cys] Gln Glu Ser Leu [Gly] Thr Ala Arg [Cys] Le

```
Asp Gly Asn Leu [Cys] Ser [Asp] Ile Asp Glu [Cys] Val Leu Ala Arg

Asp Gly Ile Ser [Cys] Phe [Asp] Ile Asp Glu [Cys] Gln Arg

Pro Gly Arg Ser [Cys] Pro [Asp] Ser Thr Ala Pro Ser Leu Leu Gly Glu Asp Gly His His Leu Asp Arg

Asp Arg [Cys] Gln Thr Arg [Asp] Leu Arg Trp Trp Glu Leu Arg
```

This includes the exact 53 amino acid residue sequence of mouse EGF (nucleotides 3281–3440), a translational start codon AUG (nucleotides 354–356) and a stop codon TAG (nucleotides 4005–4007). An open reading frame throughout the sequence which encodes for 1217 amino acid residues and a protein of approximately 133 kdal. Also, seven additional EGF-like polypeptides are identified on the basis of the homology of their amino acid sequences to EGF, especially the positional relationship of their cysteine residues, as shown below:

Human EGF Gene

A $^{32}$P-labeled (O'Farrell, *Focus* (1981) 3:1–3) 1,213 bp BstEII-PvuII fragment of mouse submaxillary EGF cDNA clone, pmEGF10, was hybridized to a human genomic DNA library (Lawn et al., *Cell* (1978) 15:1157–1174) in bacteriophage λ (available from Dr. T. Maniatis, Harvard University) using conditions which facilitate the detection of mismatched-heterologous hybrids. The BstEII-PvuII fragment of pmEGF10 encoded mouse EGF (53 amino acids) and 286 amino acids amino terminal to and 66 amino acids carboxy terminal to the EGF moiety. The hybridization conditions were 50% formamide, 5X SSC, 10% dextran sulfate, 20 mM sodium phosphate, pH 6.5, 100 μg/ml sonicated, denatured salmon testes DNA, and 0.1% sodium dodecyl sulfate at 30° C. (Wahl et al., *Proc. Natl. Acad. Sci. USA* (1979) 76:3683–3687). The filters were washed for one hour at 50° C. in 1M NaCl (Perler et al., Cell (1980) 20:555–566) before autoradiography. Four of the approximately 10$^6$ phage screened hybridized to the probe. Characterization of the human DNA inserts in these phage indicated that they represented overlapping DNA segments from the same region of the human genome. The partial sequence of the human DNA in λhEGF35, corresponding to the exons encoding EGF or uragastrone, indicated that these phage contained portions of the human EGF gene.

The human EGF gene was sequenced and the mouse and human sequences compared. The amino acid sequences of EGF from the two species are described by Carpenter, In: Tissue Growth Factors, Handbook of Experimental Pharmacology, R. Baseraga (ed.), Vol. 57, Springer-Verlag, Berlin, 1981, p. 94.

In accordance with the subject invention, polynucleotide sequences are provided which encode for a large polypeptide which includes the amino acid sequence of EGF. The large polypeptide can be used as a source of polypeptides having physiological activity. In particular, seven additional EGF-like polypeptides are identified. The DNA sequences can be used for production of the large polypeptide or fragments thereof by employing recombinant DNA technology and inserting the polypeptide sequence downstream from an appropriate promoter in a functioning episomal element. The episomal element may then be introduced into an appropriate host for replication and expression of the desired polypeptide.

Although the foregoing invention has been described in some detail by way of illustration and example for purposes of clarity of understanding, it will be obvious that certain changes and modifications may be practiced within the scope of the appended claims.

What is claimed is:

1. A composition comprising DNA molecules containing a nucleotide sequence encoding human epidermal growth factor (EGF) and substantially free of DNA molecules that do not contain said nucleotide sequence, said EGF-encoding nucleotide sequence comprising:

```
5'-AAT  AGT  GAC  TCT  GAA  TGT  CCC
   CTG  TCC  CAC  GAT  GGG  TAC  TGC
   CTC  CAT  GAT  GGT  GTG  TGC  ATC
   TAT  ATT  GAA  GCA  TTG  GAC  AAG
   TAT  GCA  TGC  AAC  TGT  GTT  GTT
   GGC  TAC  ATC  GGG  GAG  CGA  TGT
   CAG  TAC  CGA  GAC  CTG  AAG  TGG
   TGG  GAA  CTG  CGC—3'
```

2. The composition of claim 1 whrein said DNA molecules are episomal elements.

3. A composition comprising cells containing an intron free DNA sequence encoding human epidermal growth factor (EGF) substantially free of cells not containing said EGF-encoding DNA sequence, said EGF-encoding DNA sequence comprising:

```
5'-AAT  AGT  GAC  TCT  GAA  TGT  CCC
   CTG  TCC  CAC  GAT  GGG  TAC  TGC
   CTC  CAT  GAT  GGT  GTG  TGC  ATC
   TAT  ATT  GAA  GCA  TTG  GAC  AAG
   TAT  GCA  TGC  AAC  TGT  GTT  GTT
   GGC  TAC  ATC  GGG  GAG  CGA  TGT
   CAG  TAC  CGA  GAC  CTG  AAG  TGG
   TGG  GAA  CTG  CGC—3'
```

4. The composition of claim 3 wherein said cells are bacteria.

5. The composition of claim 3 wherein said cells are yeast.

* * * * *